(12) United States Patent
Kopkalli et al.

(10) Patent No.: US 9,272,968 B2
(45) Date of Patent: Mar. 1, 2016

(54) PROCESS TO SUPPRESS THE FORMATION OF 3,3,3-TRIFLUOROPROPYNE IN FLUOROCARBON MANUFACTURE

(71) Applicant: Honeywell International Inc., Morristown, NJ (US)

(72) Inventors: Haluk Kopkalli, Staten Island, NY (US); Jeffrey A. Ball, Randolph, NJ (US); Yuon Chiu, Denville, NJ (US); Hsueh Sung Tung, Getzville, NY (US); Konstantin A. Pokrovski, Orchard Park, NY (US); Daniel C. Merkel, West Seneca, NY (US)

(73) Assignee: Honeywell International Inc., Morris Plains, NJ (US)

( * ) Notice: Subject to any disclaimer, the term of this patent is extended or adjusted under 35 U.S.C. 154(b) by 133 days.

(21) Appl. No.: 13/826,627

(22) Filed: Mar. 14, 2013

(65) Prior Publication Data

US 2014/0275662 A1 Sep. 18, 2014

(51) Int. Cl.
| | |
|---|---|
| C07C 17/38 | (2006.01) |
| C07C 17/383 | (2006.01) |
| C07C 17/25 | (2006.01) |
| C07C 17/20 | (2006.01) |
| C07C 17/389 | (2006.01) |
| C07C 21/18 | (2006.01) |

(52) U.S. Cl.
CPC ............. *C07C 17/38* (2013.01); *C07B 2200/09* (2013.01); *C07C 17/206* (2013.01); *C07C 17/25* (2013.01); *C07C 17/383* (2013.01); *C07C 17/389* (2013.01)

(58) Field of Classification Search
CPC ........ C07C 17/38; C07C 17/383; C07C 21/18
USPC ................. 570/262, 177, 263, 238, 123, 153
See application file for complete search history.

(56) References Cited

U.S. PATENT DOCUMENTS

| | | | |
|---|---|---|---|
| 2,949,491 A | 8/1960 | Rucker | |
| 5,457,267 A | 10/1995 | Jansen et al. | |
| 6,166,274 A * | 12/2000 | Chen ...................... | C07C 17/00 570/160 |
| 6,844,475 B1 * | 1/2005 | Tung ..................... | C07C 17/206 570/164 |
| 7,347,980 B2 | 3/2008 | Kanno et al. | |
| 7,485,760 B2 * | 2/2009 | Wang ..................... | C01B 7/191 570/156 |
| 7,638,660 B2 | 12/2009 | Wang et al. | |
| 7,964,759 B2 | 6/2011 | Ishihara et al. | |
| 8,067,650 B2 | 11/2011 | Wang et al. | |
| 2010/0022809 A1 | 1/2010 | Cottrell et al. | |
| 2010/0145112 A1 | 6/2010 | Ishihara et al. | |
| 2011/0105807 A1 | 5/2011 | Kopkalli et al. | |

(Continued)

FOREIGN PATENT DOCUMENTS

WO  WO 2010111067 A1 *  9/2010

OTHER PUBLICATIONS

PCT ISR & Written Opinion issued in PCT/US2014/021469, dated Jun. 19, 2014.

*Primary Examiner* — Jafar Parsa
*Assistant Examiner* — Medhanit Bahta
(74) *Attorney, Agent, or Firm* — Bruce O. Bradford

(57) ABSTRACT

This invention relates to a process for the suppression of 3,3,3-trifluoropropyne during the manufacture of fluorocarbons, fluoroolefins, hydrochlorofluoroolefins. More particularly, this invention is directed to a process to suppress the formation of 3,3,3-trifluoropropyne during processes for the manufacture of HCFO-1233zd(E), HCFO-1233zd(Z), HFO-1234ze(E), and/or HFO-1234ze(Z).

17 Claims, 3 Drawing Sheets

General Scheme

(56) References Cited

U.S. PATENT DOCUMENTS

| | | |
|---|---|---|
| 2011/0201853 A1 | 8/2011 | Tung et al. |
| 2011/0295045 A1 | 12/2011 | Hulse et al. |
| 2012/0056122 A1 | 3/2012 | Hulse et al. |
| 2012/0059199 A1* | 3/2012 | Pokrovski ............ C01B 7/0706 570/155 |
| 2012/0123172 A1 | 5/2012 | Hibino et al. |
| 2012/0172636 A1* | 7/2012 | Pokrovski ............ C07C 17/206 570/135 |
| 2012/0184785 A1 | 7/2012 | Cottrell et al. |
| 2012/0271069 A1 | 10/2012 | Wang et al. |
| 2012/0271070 A1 | 10/2012 | Wang et al. |
| 2012/0296127 A1 | 11/2012 | Cottrell et al. |
| 2013/0211154 A1* | 8/2013 | Cottrell ................ C07C 17/25 570/155 |

* cited by examiner

General Scheme

Liquid phase scheme with solid desiccant

Liquid phase scheme with sulfuric acid drying

Liquid phase scheme with vapor phase sulfuric acid drying

Simplified diagram for 1233zd manufacture that avoids formation of trifluoropropyne

PROCESS TO SUPPRESS THE FORMATION OF 3,3,3-TRIFLUOROPROPYNE IN FLUOROCARBON MANUFACTURE

FIELD OF THE INVENTION

This invention relates to a process for the suppression of 3,3,3-trifluoropropyne during the manufacture of fluorocarbons, including fluoroolefins, and hydrochlorofluoroolefins. More particularly, this invention is directed to a process to suppress the formation of 3,3,3-trifluoropropyne during processes for the manufacture of HCFO-1233zd(E), HCFO-1233zd(Z), HFO-1234ze(E), and/or HFO-1234ze(Z).

BACKGROUND OF THE INVENTION

This invention especially relates to improvements in the production of HCFO-1233zd(E), HCFO-1233zd(Z), HFO-1234ze(E), and HFO-1234ze (Z). As used herein, the designations 1233zd and 1234ze will be used when either the E or Z isomers, or a combination thereof, is being referred to.

These compounds have zero or low ozone depletion potential as well as low global warming potential such that they are useful and desirable as replacements for existing materials used in refrigeration, foam blowing, solvents, monomers and other applications where other fluorocarbons are currently utilized.

Methods to produce 1233zd are known in the art. See for example US Patent Publication Nos. 2012-0172636; 2012-0271069; and 2012-0271070, which describe both 1233zd and 1234ze production processes. These documents are hereby incorporated herein by reference.

A preferred embodiment for the manufacture of 1233zd is as follows:

HCC-240fa+3HF→1233zd+4HCl which takes place in a liquid or vapor phase reaction in the absence or presence of a catalyst with large excess of HF.

Methods to produce 1234ze have also been disclosed. See for example U.S. Pat. Nos. 7,485,760 and 7,638,660 where the manufacture of 1234ze is disclosed as follows:

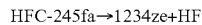

HFC-245fa→1234ze+HF which takes place in the liquid or vapor phase in the presence or absence of a dehydrofluorination catalyst. These patents are hereby incorporated herein by reference.

In the above processes to produce 1233zd and/or 1234ze, the crude product is usually a mixture of both the Z and E isomers (also known as the cis and trans isomers respectively). Typical processes employ one or more purification methods, such as distillation, extraction, decantation and absorption for purifying and recovering the desired fluoroolefin product. Since the reaction products include the acids HCl and HF depending on the process, there is a need to remove these acid components during the product purification and recovery process. Although the bulk removal of the acids is done by one or more purification techniques such as distillation, extraction, and/or decantation; one additional unit operation that is often used for the removal of residual acidity is absorption via strong caustic solutions, such as KOH, NaOH, or the like, at a pH of about 11 or higher.

Methods to produce 3,3,3-trifluoropropyne are also known in the art. See for example U.S. Pat. No. 7,964,759, which is hereby incorporated herein by reference. Disclosed in this patent is a method to produce 3,3,3-trifluoropropyne by contacting (Z)-1-halogeno-3,3,3-trifluoropropene with a high concentration of an organic or inorganic strong base (pH>10).

Both 1233zd and 1234ze are 1-halogeno-3,3,3-trifluoropropenes; 1233zd is 1-chloro-3,3,3-trifluoropropene and 1234ze is 1-fluoro-3,3,3-tetrafluoropropene.

As stated above, 3,3,3-trifluoropropyne can be formed when compounds such as 1233zd and 1234ze are allowed to react with strong bases. In processes where the desired product is one of those listed above, trifluoropropyne is usually considered to be an undesired impurity due to both potential toxicity and flammability concerns and accordingly, this compound is preferably removed if it is formed. The need for the removal of trifluoropropyne necessarily increases capital investment as well as operational costs associated with production of one or more of the above compounds. Therefore, it would be much more desirable to not form trifluoropropyne in the first place. Hence, there is a need for means by which the formation of trifluoropropyne can be avoided.

This invention provides a solution to this problem.

SUMMARY OF THE INVENTION

As shown above, 3,3,3-trifluoropropyne can be formed when crude products of 1233zd and/or 1234ze are allowed to react with a strong caustic solution. Since it is known that reaction with a strong base solution can promote the formation of trifluoropropyne, a process that does permit such a reaction, should either eliminate or reduce the formation of trifluoropropyne.

The method disclosed here is different from traditional fluorocarbon/fluoroolefin processes where unrecoverable amounts of HF and/or HCl in the crude product containing one or more of 245fa, 1234ze, 1233zd, or other intermediates in the manufacture of said compounds, is typically treated with water to remove the bulk of the acid followed by absorption of residual HF and/or HCl in a circulating caustic scrubber system (containing aqueous solution of NaOH, KOH, etc.) and finally drying the water-saturated deacidified crude product with molecular sieves and/or concentrated sulfuric acid.

In one embodiment, the crude product containing unrecoverable amounts of HF (and/or very minor amounts of HCl) is treated with water in a first HF absorber with once through water (or circulating weak HF solution) to remove the bulk of the acid. This stream would then be treated in a second absorber with once-through water to remove further amounts of acid. The essentially acid free stream which may contain trace amounts of HF would then be optionally cooled to selectively condense water to reduce the amount of moisture followed by drying/HF absorption in a circulating $H_2SO_4$ absorption system. Concentrated sulfuric acid provides a very effective means of drying fluorocarbons/fluoroolefins and, in addition, has a high affinity for HF. In addition, the sulfuric acid that is used for drying and trace HF absorption can be regenerated by means known in the art and reused in the process.

In this embodiment, the need to use a caustic scrubber is eliminated, thereby reducing the cost associated with supplying caustic to the process and the disposal of spent caustic (an aqueous mixture of caustic plus halide salts). In addition, there is a cost avoidance advantage since the prior art need to remove trifluoropropyne is eliminated.

In another embodiment, the crude product containing unrecoverable amounts of HF (and/or very minor amounts of HCl) is treated with water in a first HF absorber with once through water (or circulating weak HF solution) to remove the bulk of the acid. This stream would then be treated in a second absorber with circulating weak caustic solution between pH 7 and 10 (inclusive) to remove further amounts of acid. The acid free stream would then be optionally cooled to selectively condense water to reduce the amount of moisture followed by drying in a circulating H$_2$SO$_4$ absorption system. Concentrated sulfuric acid provides a very effective means of drying fluorocarbons/fluoroolefins. In addition, the sulfuric acid that is used for drying can be regenerated by means known in the art and reused in the process.

In another embodiment, in the production of HCFO-1233zd and/or production of HFO-1234ze the crude mixture containing both isomers of HCFO-1233zd (E and Z isomers) and/or HFO-1234ze (E and Z isomers) is first separated via distillation or other means known in the art such as extraction to recover a highly purified E isomer and a stream that is substantially Z isomer. Note, this stream may contain some E isomer but the highly purified E isomer stream should not contain more than ppm amounts of Z isomer.

Distillation is a particularly suitable method for the separation of these isomers due to boiling point differences between the E and Z isomer. For example, the boiling point of (E)-1233zd is about 19° C. while the boiling point of (Z)-1233zd is about 38° C. and the boiling point of (E)-1234ze is about −19° C. while the boiling point of (Z)-1234ze is about +9° C. The stream containing the E isomer (also known as trans isomer) could then be subjected to either the methods disclosed above, i.e., HF absorption followed by a substantially caustic-free solution which includes water and/or a weak caustic solution (pH 10 or less); or treated in the conventional manner using HF absorption followed by brief exposure to a caustic solution of any practical strength, eg., less than 4% NaOH solution.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

Various non-limiting schemes are shown to illustrate the invention.

DETAILED DESCRIPTION OF THE INVENTION

Figure 5:
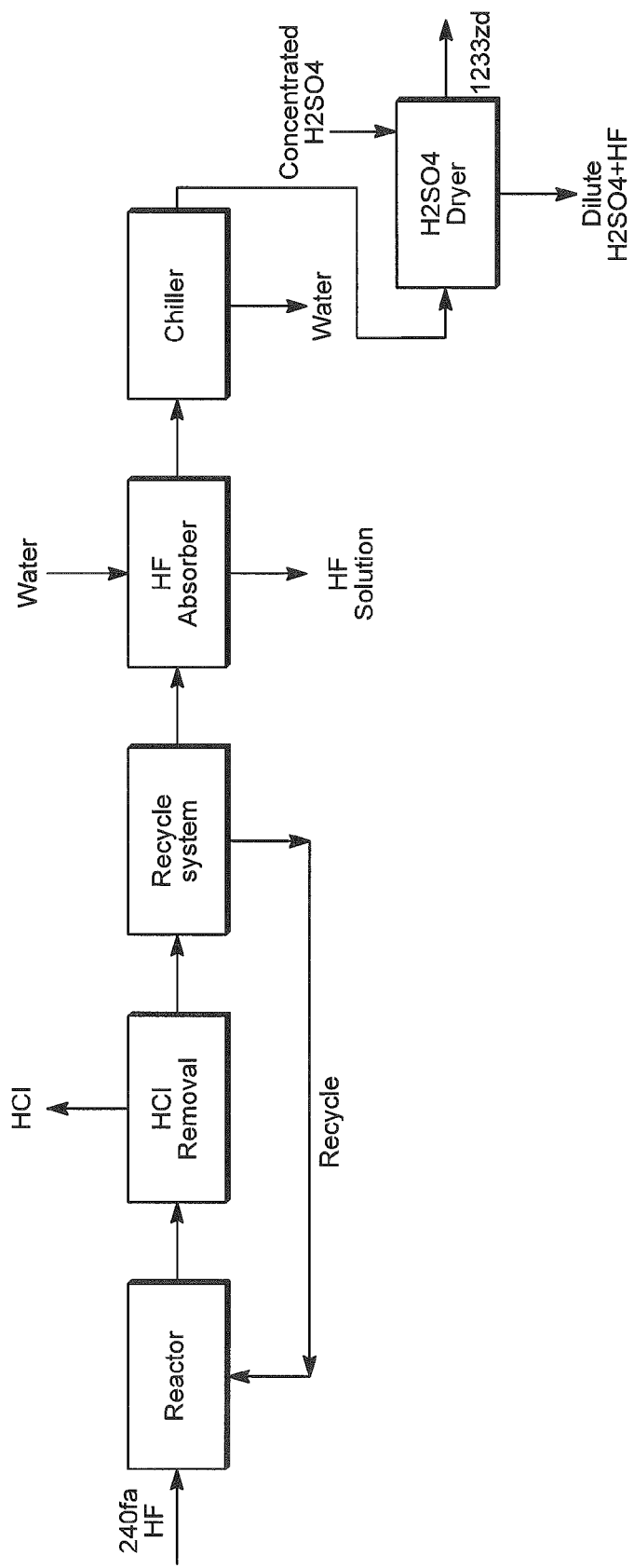
FIG. 5 shows a process for the manufacture of 1233zd with one of the embodiments of the invention herein described.

A description of one embodiment of the invention follows using a continuous 1233zd process as the example for illustration with vapor phase deacidification. This embodiment is shown in FIG. 5.

Step (1)—produce 1233zd from 240fa and excess HF by the reaction:

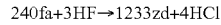

Step (2)—recover HCl and recycle intermediates and unreacted starting materials including 240fa and HF. Treat the crude 1233zd (in the vapor state) which contains HF in a water absorber using multiple stages or multiple absorbers to remove the bulk of the HF. Optionally cool the resulting vapor stream such that a portion of the water is condensed but the crude 1233zd is not condensed.

Step (3)—feed the cooled crude 1233zd (in vapor state) into a sulfuric scrubber which is circulating a concentrated sulfuric acid solution to remove both the water and any residual HF. The resulting stream which is essentially free of moisture, HF and 3,3,3-trifluoropropyne may be subjected to distillation steps to further purify the 1233zd.

The above process may also be used in a process to produce 1234ze from 245fa with no trifluoropropyne formation.

Alternative Embodiments

Figure 1:
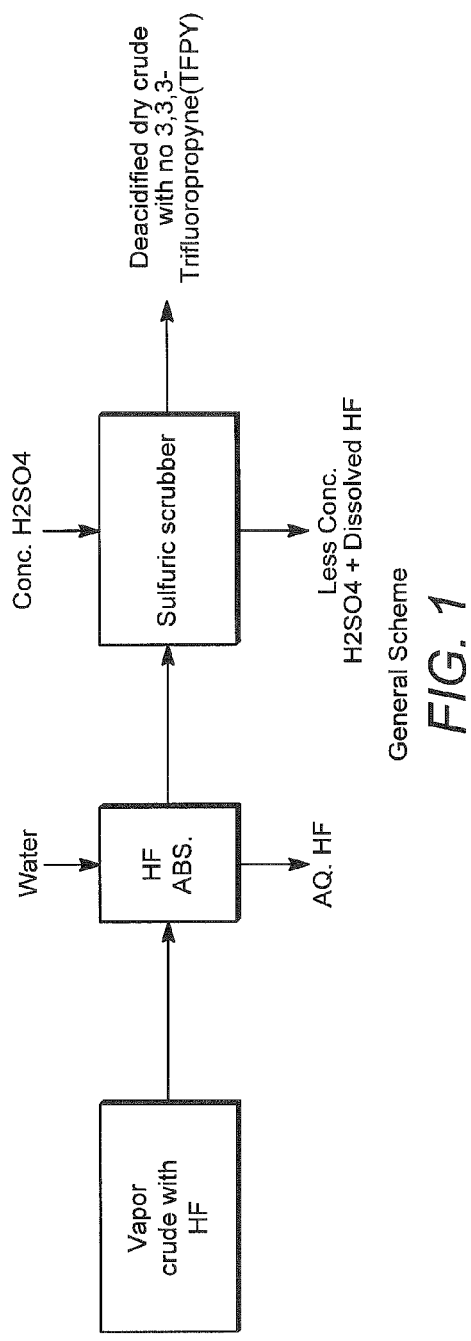
FIG. 1 shows a general scheme in the vapor phase for recovering a product with no trifluoropropyne formation.
Figure 2:
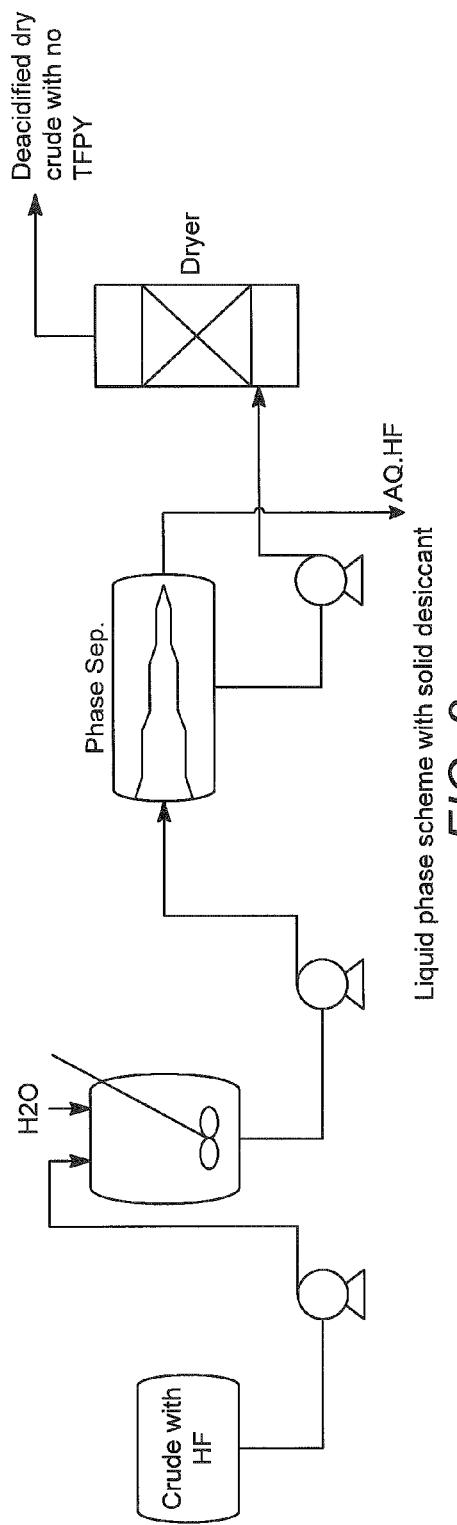
FIG. 2 shows a liquid phase scheme for deacidification with water followed by phase separation of the organic layer from the aqueous HF layer. The organic layer is then dried by passing it through a tower filled with a desiccant. The desiccant, when properly chosen, will both remove moisture and trace amounts of HF that may remain in the organic layer.

Referring to FIG. 2, a liquid phase deacidification process may also be used wherein liquid crude may be contacted with water in batch mode or in continuous mode in a single or multiple stages (FIG. 1 shows a single stage). After each stage, the organic material would be phase separated from the aqueous phase.

In another alternative embodiment, again referring to FIG. 2, continuous extraction may be used for this step. The resulting crude material which is saturated with water and trace HF may then be treated with a desiccant such as silica gel, molecular sieves or alumina which is also effective for removal of HF.

Figure 3:
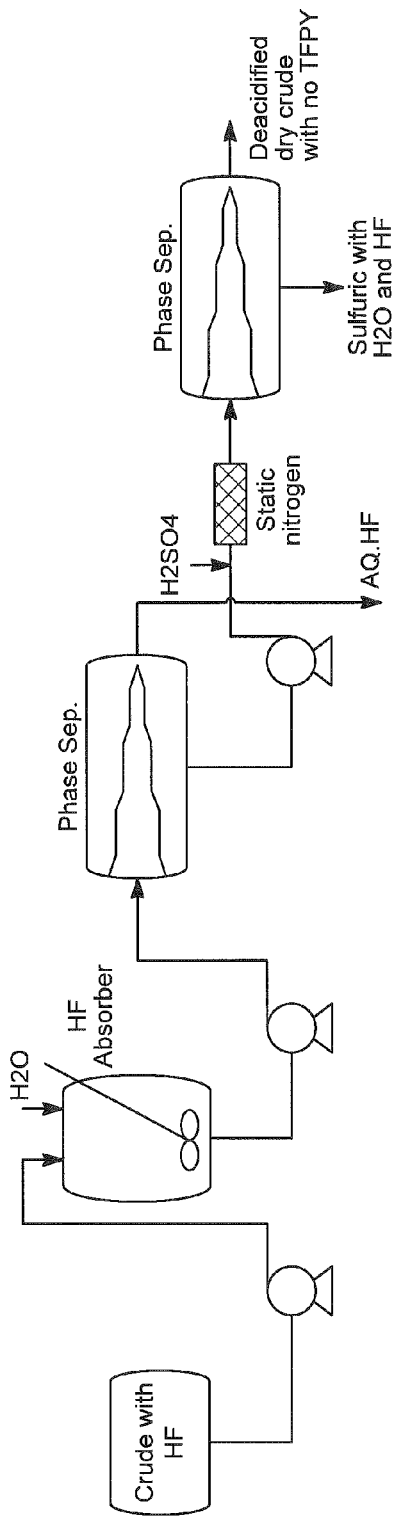
FIG. 3 shows a liquid phase scheme for deacidification with water followed by phase separation of the organic layer from the aqueous HF layer. The organic layer is then contacted with concentrated sulfuric acid to absorb moisture and trace HF.

Referring to FIG. 3, the liquid crude organic may be contacted with concentrated sulfuric acid followed by phase separation (or in an extraction column).

Figure 4:
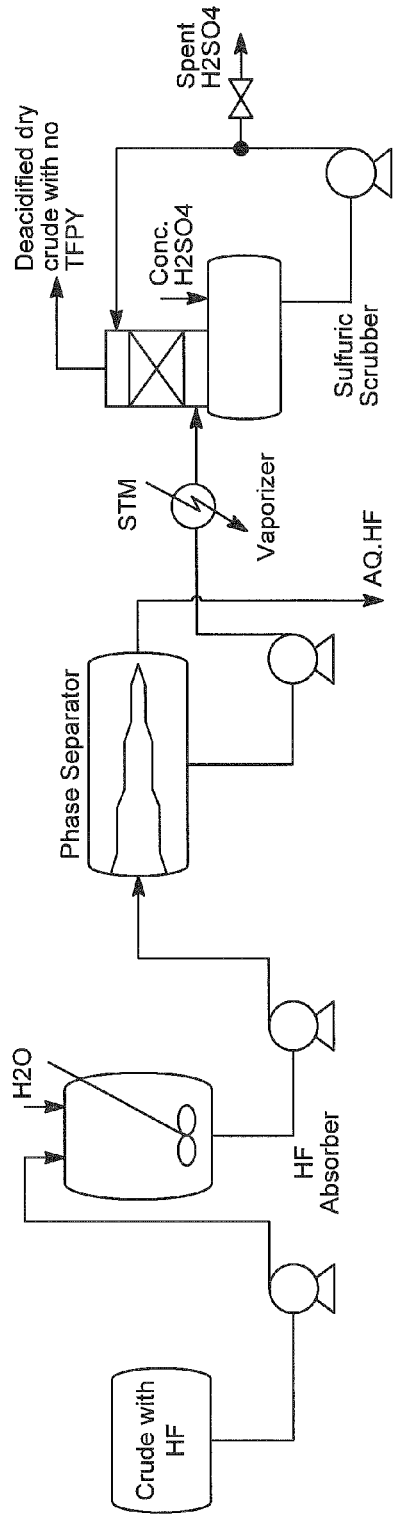
FIG. 4 shows a liquid phase scheme for deacidification with water followed by phase separation of the organic layer from the aqueous HF layer. The organic layer is then vaporized and contacted with concentrated sulfuric acid to absorb moisture and trace HF.

Referring to FIG. 4, in yet another alternative method, the liquid crude organic may first be vaporized and fed to a circulating sulfuric scrubber as described in step 5 above.

EXAMPLE 1

1233zd is produced via the methods described in the specification of US Patent Publication No. 2012-0172636, which is hereby incorporated herein by reference. The crude product contains a maximum of about 50 ppm 3,3,3-trifluoropropyne.

The crude product exiting the reactor is subjected to HCl recovery and HF recovery to recover a stream with the following composition:

| Component | wt % |
|---|---|
| 1233zd (E) | 85.4% |
| 1233zd (Z) | 4.0% |
| Other organic impurities | 7.3% |
| HCl | 0.1% |

-continued

| Component | wt % |
|---|---|
| HF | 3.2% |
| 3,3,3-trifluoropropyne | <50 ppm |

The temperature of the feed stream is approximately 46° C. and the pressure is approximately 10 psig.

The above stream is fed to an HF Absorber which has a supply of once-through fresh water feed at ambient temperature (approximately 25° to 30° C.). The HF Absorber is packed with random packing and has sufficient theoretical stages for absorbing at least 99% of the incoming HF. The amount of water is adjusted to produce a nominal 5% solution of aqueous HF as well as supply sufficient wetting of the packing. The stream exiting the HF absorber, which is saturated with water, is cooled to in order to condense some portion of the water. The resulting stream is continuously fed to a sulfuric acid dryer to remove the remaining moisture and trace HF. The sulfuric acid dryer consists of a pump tank which is initially filled with 99+ wt % $H_2SO_4$ connected to a packed tower. A pump is used to circulate the $H_2SO_4$ from the pump tank to the top of the packed tower while the process stream flows upwards.

The stream exiting the top of the sulfuric acid dryer is analyzed and found to contain no additional 3,3,3-trifluoropropyne.

EXAMPLE 2

99.9% pure 1233zd(E) was passed through a scrubber (dimensions of the scrubber column: 6 inch diameter, 10 foot height) circulating dilute NaOH solution at pH 10. The feed rate of 1233zd(E) was maintained at 1-2 lbs/hr. The product exiting the scrubber was passed through a Drierite ($CaSO_4$) drier and sampled. No 3,3,3-trifluoropropyne was observed in the collected samples.

EXAMPLE 3

Example 2 was repeated except the pH of circulating solution was about 8. Again, as in Example 2, no 3,3,3-trifluoropropyne was observed in the collected after scrubber and drier samples.

COMPARATIVE EXAMPLE 1

1233zd was produced via the methods described in the specification of US Patent Publication No. 2012-0172636, the disclosure of which is hereby incorporated herein by reference. The crude product contains a maximum of about 50 ppm 3,3,3-trifluoropropyne.

The crude product exiting the reactor had the following composition:

| Component | wt % |
|---|---|
| 1233zd (E) | 32.2% |
| 1233zd (Z) | 1.5% |
| Other organic impurities | 2.8% |
| HCl | 39.9% |
| HF | 23.6% |
| 3,3,3-trifluoropropyne | <40 ppm |

The organic composition in the above is the same as in Example 1. What differs is the amount of HF and HCl because the reaction product was not subjected to HCl and HF recovery. The wt. percent of the composition of the stream exiting the reactor represented in the above Table is based on about 4.4 moles of organics (average molecular weight about 140 g/mole), about 18.5 moles of HCl, and about 20 moles of HF.

The stream exiting the reactor was passed through a continuous caustic scrubber column. A 10% KOH solution was continuously circulated through the column at about 50° to 65° C. to remove excess of HF and HCl by-product. Acid free crude product that exited the scrubber column was then dried using Drierite ($CaSO_4$). The crude product exiting the drier was analyzed and the concentration of 3,3,3-trifluoropropyne was found to be from 0.4 wt % to 0.7 wt %.

COMPARATIVE EXAMPLE 2

1233zd is produced via the methods described in the specification of US Patent Publication No. 2012-0172636, the disclosure of which is hereby incorporated herein by reference. The crude product contains a maximum of about 50 ppm 3,3,3-trifluoropropyne.

The crude product exiting the reactor is subjected to HCl recovery and HF recovery to recover a stream with the following composition:

| Component | wt % |
|---|---|
| 1233zd (E) | 85.4% |
| 1233zd (Z) | 4.0% |
| Other organic impurities | 7.3% |
| HCl | 0.1% |
| HF | 3.2% |
| 3,3,3-trifluoropropyne | <40 ppm |

The temperature of the feed stream is approximately 46° C. and the pressure is approximately 10 psig.

The above stream is fed to a circulating caustic scrubber which has an initial concentration of 4 wt % NaOH. The stream exiting the circulating caustic scrubber, which is saturated with water, is cooled to in order to condense some portion of the water. The resulting stream is continuously fed to a sulfuric acid dryer to remove the remaining moisture. The sulfuric acid dryer consists of a pump tank which is initially filled with 99+ wt % $H_2SO_4$ connected to a packed tower. A pump is used to circulate the $H_2SO_4$ from the pump tank to the top of the packed tower while the process stream flows upwards. The stream exiting the top of the sulfuric acid dryer is analyzed and found to contain from about 800 to 2000 ppm 3,3,3-trifluoropropyne.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for preventing the formation of 3,3,3-trifluoropropyne during the manufacture of fluorocarbon compounds, said method comprising the steps of:
   (a) forming a fluorocarbon compound selected from the group consisting of HCFO-1233zd(Z) and HFO-1234ze(Z) in a reaction process that generates reaction products comprising one or more acids;
   (b) conducting one or more substantially caustic-free bulk acid removal procedures on the reaction products of step (a);
   wherein the bulk removal of the acids in step (b) comprises treating the reaction products with a first scrubber solution in a first absorber to remove the bulk of the acid; and
   (c) conducting one or more trace acid removal procedures to remove acids remaining after step (b); and
   whereby the formation of 3,3,3-trifluoropropyne is prevented by the removal of acid during the process.

2. The process of claim 1, wherein the bulk removal of the acids in step (b) further comprises one or more purification techniques selected from distillation, extraction, and decantation.

3. The process of claim 1, wherein the first scrubber solution comprises water.

4. The process of claim 1, wherein the acid being removed is HF and the first scrubber solution comprises a weak HF solution.

5. The process of claim 1, wherein the first scrubber solution comprises $H_2SO_4$.

6. The process of claim 1, whereby in step (c) the reaction products of step (b) are treated in a second absorber with a second scrubber solution to remove further amounts of acid.

7. The process of claim 6, wherein the second scrubber solution comprises water.

8. The process of claim 6, wherein the second scrubber solution comprises $H_2SO_4$.

9. The process of claim 1, wherein step (b) comprises a liquid phase deacidification process, using water to absorb and remove the bulk of the acid.

10. The process of claim 9, wherein the step (b) process is conducted in batch mode.

11. The process of claim 10, wherein the step (b) process is conducted in a single stage.

12. The process of claim 10, wherein the step (b) process is conducted in multiple stages.

13. The process of claim 10, wherein the step (b) process is conducted in continuous mode.

14. The process of claim 13, wherein the step (b) process is conducted in a single stage.

15. The process of claim 13, wherein the step (b) process is conducted in multiple stages.

16. The process of claim 10, wherein the step (b) process further comprises a continuous extraction procedure.

17. A process for preventing the formation of 3,3,3-trifluoro-propyne during the manufacture of fluorocarbon compounds, said method comprising the steps of:
   (a) forming a fluorocarbon compound selected from the group consisting of HCFO-1233zd(Z) and HFO-1234ze(Z) in a reaction process that generates reaction products comprising one or more acids;
   (b) conducting one or more substantially caustic-free bulk acid removal procedures on the reaction products of step (a);
   wherein the bulk removal of the acids in step (b) comprises treating the reaction products with a first scrubber solution selected from water and an aqueous HF solution in a first absorber to remove the bulk of the acid; and
   (c) conducting one or more trace acid removal procedures to remove acids remaining after step (b);
   wherein in step (c) the reaction products of step (b) are treated in a second absorber with a second scrubber solution selected from water and $H_2SO_4$ to remove further amounts of acid; and
   whereby the formation of 3,3,3-trifluoropropyne is prevented by the removal of acid during the process.

* * * * *